US008722370B2

(12) United States Patent
Filippov et al.

(10) Patent No.: US 8,722,370 B2
(45) Date of Patent: May 13, 2014

(54) METHOD FOR PRODUCING AN L-AMINO ACID USING A BACTERIUM OF THE ENTEROBACTERIACEAE FAMILY, HAVING ATTENUATED EXPRESSION OF GENE(S) ENCODING PEPTIDASE

(71) Applicant: AJINOMOTO CO., INC., Tokyo (JP)

(72) Inventors: Dmitriy Vladimirovich Filippov, Moscow (RU); Tatyana Viktorovna Leonova, Moscow (RU); Elvira Borisovna Voroshilova, Moscow (RU); Mikhail Markovich Gusyatiner, Moscow (RU); Mika Moriya, Kanagawa (JP); Yuri Nagai, Kanagawa (JP); Keiko Noguchi, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/687,541

(22) Filed: Nov. 28, 2012

(65) Prior Publication Data
US 2013/0078682 A1 Mar. 28, 2013

Related U.S. Application Data

(63) Continuation of application No. PCT/JP2011/063301, filed on Jun. 3, 2011.

(30) Foreign Application Priority Data

Jun. 3, 2010 (RU) .................................. 2010122647

(51) Int. Cl.
*C12P 13/10* (2006.01)
(52) U.S. Cl.
USPC ........................................................ 435/114
(58) Field of Classification Search
None
See application file for complete search history.

(56) References Cited

U.S. PATENT DOCUMENTS

| | | | |
|---|---|---|---|
| 4,278,765 A | 7/1981 | Debabov et al. | |
| 4,346,170 A | 8/1982 | Sano et al. | |
| 5,661,012 A | 8/1997 | Sano et al. | |
| 6,040,160 A | 3/2000 | Kojima et al. | |
| 7,531,332 B2 | 5/2009 | Livshits et al. | |
| 7,618,803 B2 | 11/2009 | Tabolina et al. | |
| 7,618,804 B2 | 11/2009 | Tabolina et al. | |
| 7,771,976 B2 | 8/2010 | Gulevich et al. | |
| 7,794,988 B2 | 9/2010 | Filippov et al. | |
| 7,803,584 B2 | 9/2010 | Rybak et al. | |
| 7,855,060 B2 | 12/2010 | Filippov et al. | |
| 7,888,077 B2 | 2/2011 | Filippov et al. | |
| 7,915,018 B2 | 3/2011 | Rybak et al. | |
| 7,919,282 B2 | 4/2011 | Rybak et al. | |
| 7,919,283 B2 | 4/2011 | Filippov et al. | |
| 8,003,367 B2 | 8/2011 | Marchenko et al. | |
| 8,003,368 B2 | 8/2011 | Marchenko et al. |
| 8,030,036 B2 | 10/2011 | Van Dien et al. |
| 8,088,606 B2 | 1/2012 | Rybak et al. |
| 8,114,639 B2 | 2/2012 | Filippov et al. |
| 8,137,938 B2 | 3/2012 | Nagai et al. |
| 8,227,214 B2 | 7/2012 | Rybak et al. |
| 2003/0148475 A1 | 8/2003 | Ptitsyn et al. |
| 2005/0026258 A1 | 2/2005 | Ptitsyn et al. |
| 2009/0130708 A1 | 5/2009 | Hashimoto et al. |
| 2009/0137011 A1 | 5/2009 | Filippov et al. |
| 2010/0047878 A1 | 2/2010 | Nagai et al. |
| 2010/0143983 A1 | 6/2010 | Kiryukhin et al. |
| 2011/0143403 A1 | 6/2011 | Rybak et al. |
| 2012/0040415 A1 | 2/2012 | Nakahara et al. |
| 2012/0219996 A1 | 8/2012 | Rybak et al. |
| 2012/0237986 A1 | 9/2012 | Ziyatdinov et al. |

FOREIGN PATENT DOCUMENTS

EP 1 870 457 12/2007

OTHER PUBLICATIONS

Charlier, D., et al., "carP, Involved in Pyrimidine Regulation of the *Escherichia coli* Carbamoylphosphate Synthetase Operon Encodes a Sequence-specific DNA-binding Protein Identical to XerB and PepA, also Required for Resolution of ColE1 Multimers," J. Mol. Biol. 1995;250:392-406.

Charlier, D., et al., "Mutational Analysis of *Escherichia coli* PepA, a Multifunctional DNA-binding Aminopeptidase," J. Mol. Biol. 2000;302:411-426.

Henrich, B., et al., "The promoter region of the *Escherichia coli* pepD gene: deletion analysis and control by phosphate concentration," Mol. Gen. Genet. 1992;232(1):117-125.

Hermsdorf, C. L., et al., "Soluble Di- and Aminopeptidases in *Escherichia coli* K-12," Int. J. Peptide Protein Res. 1979;13:146-151.

Klein, J., et al., "Cloning and Expression of the *pepD* Gene of *Escherichia coli*," J. Gen. Microbiol. 1986;132:2337-2343.

Nguyen Le Minh, P., et al., "Insights into the architecture and stoichiometry of *Escherichia coli* PepA-DNA complexes involved in transcriptional control and site-specific DNA recombination by atomic force microscopy," Nucl. Acids Res. 2009;37(5):1463-1476.

Roovers, M., et al., "carP, a Novel Gene Regulating the Transcription of the Carbamoylphosphate Synthetase Operon of *Escherichia coli*," J. Mol. Biol. 1988;204:857-865.

Schroeder, U., et al., "Peptidase D of *Escherichia coli* K-12, a metal-lopeptidase of low substrate specificity," FEMS Microbiol. Lett. 1994;123:153-160.

(Continued)

*Primary Examiner* — Suzanne M Noakes
(74) *Attorney, Agent, or Firm* — Shelly Guest Cermak; Cermak Nakajima LLP

(57) ABSTRACT

The present invention provides a method for producing L-amino acids, such as L-arginine, L-citrulline, and L-lysine, using a bacterium of the Enterobacteriaceae family, particularly a bacterium belonging to the genus *Escherichia* or *Pantoea*, which has been modified to attenuate expression of one or more genes, such as the pepA, pepB, and pepD genes.

6 Claims, 2 Drawing Sheets

(56) References Cited

OTHER PUBLICATIONS

Stirling, C. J., et al., "xerB, an *Escherichia coli* gene required for plasmid ColE1 site-specific recombination, is identical to *pepA*, encoding aminopeptidase A, a protein with substantial similarity to bovine lens leucine aminopeptidase," The EMBO Journal 1989;8(5):1623-1627.

Suzuki, H., et al., "Aminopeptidases A, B, and N and Dipeptidase D Are the Four Cysteinylglycinases of *Escherichia coli* K-12," J. Bacteriol. 2001;183(4):1489-1490.

Suzuki, H., et al., "Purification and Characterization of Aminopeptidase B from *Escherichia coli* K-12," Biosci. Biotechnol. Biochem. 2001;65(7):1549-1558.

Tabata, K., et al., "Fermentative Production of L-Alanyl-L-Glutamine by a Metabolically Engineered *Escherichia coli* Strain Expressing L-Amino Acid α-Ligase," Appl. Environmen. Microbiol. 2007;73(20):6378-6385.

Tuchman, M., et al., "Enhanced Production of Arginine and Urea by Genetically Engineered *Escherichia coli* K-12 Strains," Appl. Environmen. Microbiol. 1997;63(1):33-38.

International Search Report for PCT Patent App. No. PCT/JP2011/063301 (Sep. 13, 2012).

SEQUENCE LISTING

<160> NUMBER OF SEQ ID NOS: 16

<210> SEQ ID NO 1
<211> LENGTH: 1512
<212> TYPE: DNA
<213> ORGANISM: Escherichia coli -continued

```
<220> FEATURE:
<221> NAME/KEY: CDS
<222> LOCATION: (1)..(1512)

<400> SEQUENCE: 1 atg gag ttt agt gta aaa agc ggt agc ccg gag aaa cag cgg agt gcc      48
Met Glu Phe Ser Val Lys Ser Gly Ser Pro Glu Lys Gln Arg Ser Ala
1               5                   10                  15 tgc atc gtc gtg ggc gtc ttc gaa cca cgt cgc ctt tct ccg att gca      96
Cys Ile Val Val Gly Val Phe Glu Pro Arg Arg Leu Ser Pro Ile Ala
            20                  25                  30 gaa cag ctc gat aaa atc agc gat ggg tac atc agc gcc ctg cta cgt     144
Glu Gln Leu Asp Lys Ile Ser Asp Gly Tyr Ile Ser Ala Leu Leu Arg
        35                  40                  45 cgg ggc gaa ctg gaa gga aaa ccg ggg cag aca ttg ttg ctg cac cat     192
Arg Gly Glu Leu Glu Gly Lys Pro Gly Gln Thr Leu Leu Leu His His
    50                  55                  60 gtt ccg aat gta ctt tcc gag cga att ctc ctt att ggt tgc ggc aaa     240
Val Pro Asn Val Leu Ser Glu Arg Ile Leu Leu Ile Gly Cys Gly Lys
65                  70                  75                  80 gaa cgt gag ctg gat gag cgt cag tac aag cag gtt att cag aaa acc     288
Glu Arg Glu Leu Asp Glu Arg Gln Tyr Lys Gln Val Ile Gln Lys Thr
                85                  90                  95 att aat acg ctg aat gat act ggc tca atg gaa gcg gtc tgc ttt ctg     336
Ile Asn Thr Leu Asn Asp Thr Gly Ser Met Glu Ala Val Cys Phe Leu
            100                 105                 110 act gag ctg cac gtt aaa ggc cgt aac aac tac tgg aaa gtg cgt cag     384
Thr Glu Leu His Val Lys Gly Arg Asn Asn Tyr Trp Lys Val Arg Gln
        115                 120                 125 gct gtc gag acg gca aaa gag acg ctc tac agt ttc gat cag ctg aaa     432
Ala Val Glu Thr Ala Lys Glu Thr Leu Tyr Ser Phe Asp Gln Leu Lys
    130                 135                 140 acg aac aag agc gaa ccg cgt cgt ccg ctg cgt aag atg gtg ttc aac     480
Thr Asn Lys Ser Glu Pro Arg Arg Pro Leu Arg Lys Met Val Phe Asn
145                 150                 155                 160 gtg ccg acc cgc cgt gaa ctg acc agc ggt gag cgc gcg atc cag cac     528
Val Pro Thr Arg Arg Glu Leu Thr Ser Gly Glu Arg Ala Ile Gln His
                165                 170                 175 ggt ctg gcg att gcc gcc ggg att aaa gca gca aaa gat ctc ggc aat     576
Gly Leu Ala Ile Ala Ala Gly Ile Lys Ala Ala Lys Asp Leu Gly Asn
            180                 185                 190 atg ccg ccg aat atc tgt aac gcc gct tac ctc gct tca caa gcg cgc     624
Met Pro Pro Asn Ile Cys Asn Ala Ala Tyr Leu Ala Ser Gln Ala Arg
        195                 200                 205 cag ctg gct gac agc tac agc aag aat gtc atc acc cgc gtt atc ggc     672
Gln Leu Ala Asp Ser Tyr Ser Lys Asn Val Ile Thr Arg Val Ile Gly
    210                 215                 220 gaa cag cag atg aaa gag ctg ggg atg cat tcc tat ctg gcg gtc ggt     720
Glu Gln Gln Met Lys Glu Leu Gly Met His Ser Tyr Leu Ala Val Gly
225                 230                 235                 240 cag ggt tcg caa aac gaa tcg ctg atg tcg gtg att gag tac aaa ggc     768
Gln Gly Ser Gln Asn Glu Ser Leu Met Ser Val Ile Glu Tyr Lys Gly
                245                 250                 255 aac gcg tcg gaa gat gca cgc cca atc gtg ctg gtg ggt aaa ggt tta     816
Asn Ala Ser Glu Asp Ala Arg Pro Ile Val Leu Val Gly Lys Gly Leu
            260                 265                 270 acc ttc gac tcc ggc ggt atc tcg atc aag cct tca gaa ggc atg gat     864
Thr Phe Asp Ser Gly Gly Ile Ser Ile Lys Pro Ser Glu Gly Met Asp
        275                 280                 285 gag atg aag tac gat atg tgc ggt gcg gca gcg gtt tac ggc gtg atg     912
Glu Met Lys Tyr Asp Met Cys Gly Ala Ala Ala Val Tyr Gly Val Met
```

```
                    290                 295                 300
cgg atg gtc gcg gag cta caa ctg ccg att aac gtt atc ggc gtg ttg    960
Arg Met Val Ala Glu Leu Gln Leu Pro Ile Asn Val Ile Gly Val Leu
305                 310                 315                 320 gca ggc tgc gaa aac atg cct ggc gga cga gcc tat cgt ccg ggc gat   1008
Ala Gly Cys Glu Asn Met Pro Gly Gly Arg Ala Tyr Arg Pro Gly Asp
                325                 330                 335 gtg tta acc acc atg tcc ggt caa acc gtt gaa gtg ctg aac acc gac   1056
Val Leu Thr Thr Met Ser Gly Gln Thr Val Glu Val Leu Asn Thr Asp
    340                 345                 350 gct gaa ggc cgc ctg gta ctg tgc gac gtg tta act tac gtt gag cgt   1104
Ala Glu Gly Arg Leu Val Leu Cys Asp Val Leu Thr Tyr Val Glu Arg
355                 360                 365 ttt gag ccg gaa gcg gtg att gac gtg gcg acg ctg acc ggt gcc tgc   1152
Phe Glu Pro Glu Ala Val Ile Asp Val Ala Thr Leu Thr Gly Ala Cys
370                 375                 380 gtg atc gcg ctg ggt cat cat att act ggt ctg atg gcg aac cat aat   1200
Val Ile Ala Leu Gly His His Ile Thr Gly Leu Met Ala Asn His Asn
385                 390                 395                 400 ccg ctg gcc cat gaa ctg att gcc gcg tct gaa caa tcc ggt gac cgc   1248
Pro Leu Ala His Glu Leu Ile Ala Ala Ser Glu Gln Ser Gly Asp Arg
                405                 410                 415 gca tgg cgc tta ccg ctg ggt gac gag tat cag gaa caa ctg gag tcc   1296
Ala Trp Arg Leu Pro Leu Gly Asp Glu Tyr Gln Glu Gln Leu Glu Ser
            420                 425                 430 aat ttt gcc gat atg gcg aac att ggc ggt cgt cct ggt ggg gcg att   1344
Asn Phe Ala Asp Met Ala Asn Ile Gly Gly Arg Pro Gly Gly Ala Ile
        435                 440                 445 acc gca ggt tgc ttc ctg tca cgc ttt acc cgt aag tac aac tgg gcg   1392
Thr Ala Gly Cys Phe Leu Ser Arg Phe Thr Arg Lys Tyr Asn Trp Ala
    450                 455                 460 cac ctg gat atc gcc ggt acc gcc tgg cgt tct ggt aaa gca aaa ggc   1440
His Leu Asp Ile Ala Gly Thr Ala Trp Arg Ser Gly Lys Ala Lys Gly
465                 470                 475                 480 gcc acc ggt cgt ccg gta gcg ttg ctg gca cag ttc ctg tta aac cgc   1488
Ala Thr Gly Arg Pro Val Ala Leu Leu Ala Gln Phe Leu Leu Asn Arg
                485                 490                 495 gct ggg ttt aac ggc gaa gag taa                                    1512
Ala Gly Phe Asn Gly Glu Glu
            500

<210> SEQ ID NO 2
<211> LENGTH: 503
<212> TYPE: PRT
<213> ORGANISM: Escherichia coli

<400> SEQUENCE: 2

Met Glu Phe Ser Val Lys Ser Gly Ser Pro Glu Lys Gln Arg Ser Ala
1               5                   10                  15

Cys Ile Val Val Gly Val Phe Glu Pro Arg Arg Leu Ser Pro Ile Ala
                20                  25                  30

Glu Gln Leu Asp Lys Ile Ser Asp Gly Tyr Ile Ser Ala Leu Leu Arg
            35                  40                  45

Arg Gly Glu Leu Glu Gly Lys Pro Gly Gln Thr Leu Leu Leu His His
        50                  55                  60

Val Pro Asn Val Leu Ser Glu Arg Ile Leu Ile Gly Cys Gly Lys
65                  70                  75                  80

Glu Arg Glu Leu Asp Glu Arg Gln Tyr Lys Gln Val Ile Gln Lys Thr
                85                  90                  95
```

-continued

```
Ile Asn Thr Leu Asn Asp Thr Gly Ser Met Glu Ala Val Cys Phe Leu
            100                 105                 110

Thr Glu Leu His Val Lys Gly Arg Asn Asn Tyr Trp Lys Val Arg Gln
        115                 120                 125

Ala Val Glu Thr Ala Lys Glu Thr Leu Tyr Ser Phe Asp Gln Leu Lys
    130                 135                 140

Thr Asn Lys Ser Glu Pro Arg Arg Pro Leu Arg Lys Met Val Phe Asn
145                 150                 155                 160

Val Pro Thr Arg Arg Glu Leu Thr Ser Gly Glu Arg Ala Ile Gln His
                165                 170                 175

Gly Leu Ala Ile Ala Ala Gly Ile Lys Ala Ala Lys Asp Leu Gly Asn
            180                 185                 190

Met Pro Pro Asn Ile Cys Asn Ala Ala Tyr Leu Ala Ser Gln Ala Arg
        195                 200                 205

Gln Leu Ala Asp Ser Tyr Ser Lys Asn Val Ile Thr Arg Val Ile Gly
    210                 215                 220

Glu Gln Gln Met Lys Glu Leu Gly Met His Ser Tyr Leu Ala Val Gly
225                 230                 235                 240

Gln Gly Ser Gln Asn Glu Ser Leu Met Ser Val Ile Glu Tyr Lys Gly
                245                 250                 255

Asn Ala Ser Glu Asp Ala Arg Pro Ile Val Leu Val Gly Lys Gly Leu
            260                 265                 270

Thr Phe Asp Ser Gly Gly Ile Ser Ile Lys Pro Ser Glu Gly Met Asp
        275                 280                 285

Glu Met Lys Tyr Asp Met Cys Gly Ala Ala Val Tyr Gly Val Met
    290                 295                 300

Arg Met Val Ala Glu Leu Gln Leu Pro Ile Asn Val Ile Gly Val Leu
305                 310                 315                 320

Ala Gly Cys Glu Asn Met Pro Gly Gly Arg Ala Tyr Arg Pro Gly Asp
                325                 330                 335

Val Leu Thr Thr Met Ser Gly Gln Thr Val Glu Val Leu Asn Thr Asp
            340                 345                 350

Ala Glu Gly Arg Leu Val Leu Cys Asp Val Leu Thr Tyr Val Glu Arg
        355                 360                 365

Phe Glu Pro Glu Ala Val Ile Asp Val Ala Thr Leu Thr Gly Ala Cys
    370                 375                 380

Val Ile Ala Leu Gly His His Ile Thr Gly Leu Met Ala Asn His Asn
385                 390                 395                 400

Pro Leu Ala His Glu Leu Ile Ala Ala Ser Glu Gln Ser Gly Asp Arg
                405                 410                 415

Ala Trp Arg Leu Pro Leu Gly Asp Glu Tyr Gln Glu Gln Leu Glu Ser
            420                 425                 430

Asn Phe Ala Asp Met Ala Asn Ile Gly Gly Arg Pro Gly Gly Ala Ile
        435                 440                 445

Thr Ala Gly Cys Phe Leu Ser Arg Phe Thr Arg Lys Tyr Asn Trp Ala
    450                 455                 460

His Leu Asp Ile Ala Gly Thr Ala Trp Arg Ser Gly Lys Ala Lys Gly
465                 470                 475                 480

Ala Thr Gly Arg Pro Val Ala Leu Leu Ala Gln Phe Leu Leu Asn Arg
                485                 490                 495

Ala Gly Phe Asn Gly Glu Glu
            500
```

<210> SEQ ID NO 3

```
<211> LENGTH: 60
<212> TYPE: DNA
<213> ORGANISM: Artificial sequence
<220> FEATURE:
<223> OTHER INFORMATION: primer P1

<400> SEQUENCE: 3
caccgccgtt gtctttaaga ttcaggagcg tagtgccgct caagttagta taaaaaagct    60

<210> SEQ ID NO 4
<211> LENGTH: 60
<212> TYPE: DNA
<213> ORGANISM: Artificial sequence
<220> FEATURE:
<223> OTHER INFORMATION: primer P2

<400> SEQUENCE: 4
cgccgcatcc ggcaataaca gccttgcctg acgcaatgaa gcctgccttt ttatactaag    60

<210> SEQ ID NO 5
<211> LENGTH: 20
<212> TYPE: DNA
<213> ORGANISM: Artificial sequence
<220> FEATURE:
<223> OTHER INFORMATION: primer P3

<400> SEQUENCE: 5
agttcagtgc tgtgtaggtc                                                20

<210> SEQ ID NO 6
<211> LENGTH: 20
<212> TYPE: DNA
<213> ORGANISM: Artificial sequence
<220> FEATURE:
<223> OTHER INFORMATION: primer P4

<400> SEQUENCE: 6
atcgcaacag cggacatgag                                                20

<210> SEQ ID NO 7
<211> LENGTH: 1284
<212> TYPE: DNA
<213> ORGANISM: Escherichia coli
<220> FEATURE:
<221> NAME/KEY: CDS
<222> LOCATION: (1)..(1284)

<400> SEQUENCE: 7 atg aca gaa gcg atg aag att acc ctc tct acc caa cct gcc gac gcg    48
Met Thr Glu Ala Met Lys Ile Thr Leu Ser Thr Gln Pro Ala Asp Ala
1               5                   10                  15 cgc tgg gga gaa aaa gca act tac agc att aat aat gac ggc att acc    96
Arg Trp Gly Glu Lys Ala Thr Tyr Ser Ile Asn Asn Asp Gly Ile Thr
            20                  25                  30 ctg cat ttg aac ggg gca gac gat ctg ggg ctg atc cag cgt gcg gcg   144
Leu His Leu Asn Gly Ala Asp Asp Leu Gly Leu Ile Gln Arg Ala Ala
        35                  40                  45 cgc aag att gac ggt ctg ggc atc aag cat gtt cag tta agc ggt gaa   192
Arg Lys Ile Asp Gly Leu Gly Ile Lys His Val Gln Leu Ser Gly Glu
    50                  55                  60 ggc tgg gat gcg gat cgc tgc tgg gca ttc tgg caa ggt tac aaa gcc   240
Gly Trp Asp Ala Asp Arg Cys Trp Ala Phe Trp Gln Gly Tyr Lys Ala
65                  70                  75                  80 ccg aaa ggc acg cgt aaa gtg gtg tgg ccg gat ctg gac gat gcc cag   288
Pro Lys Gly Thr Arg Lys Val Val Trp Pro Asp Leu Asp Asp Ala Gln
                85                  90                  95
```

```
cgc cag gaa ctg gat aac cgc ctg atg atc atc gac tgg gtg cgt gac         336
Arg Gln Glu Leu Asp Asn Arg Leu Met Ile Ile Asp Trp Val Arg Asp
        100                 105                 110 acc atc aac gca ccg gca gaa gaa ttg gga cca tcg caa ctg gca cag         384
Thr Ile Asn Ala Pro Ala Glu Glu Leu Gly Pro Ser Gln Leu Ala Gln
        115                 120                 125 cgt gct gtt gat ctg atc agc aac gtc gcg ggc gat cgt gtg act tat         432
Arg Ala Val Asp Leu Ile Ser Asn Val Ala Gly Asp Arg Val Thr Tyr
130                 135                 140 cgg atc acc aaa ggc gaa gat ctg cgt gag caa ggt tat atg ggg ctg         480
Arg Ile Thr Lys Gly Glu Asp Leu Arg Glu Gln Gly Tyr Met Gly Leu
145                 150                 155                 160 cac aca gtc gga cgc ggt tca gaa cgt tct ccg gta ttg ctg gcg ctg         528
His Thr Val Gly Arg Gly Ser Glu Arg Ser Pro Val Leu Leu Ala Leu
                165                 170                 175 gat tac aac cca act ggc gat aaa gaa gcg cca gtg tac gcg tgc ctg         576
Asp Tyr Asn Pro Thr Gly Asp Lys Glu Ala Pro Val Tyr Ala Cys Leu
        180                 185                 190 gta ggt aaa ggt atc act ttt gac tcc ggc ggc tac agc atc aaa cag         624
Val Gly Lys Gly Ile Thr Phe Asp Ser Gly Gly Tyr Ser Ile Lys Gln
        195                 200                 205 act gcg ttt atg gac tcg atg aag tcg gac atg ggc ggc gcg gca acg         672
Thr Ala Phe Met Asp Ser Met Lys Ser Asp Met Gly Gly Ala Ala Thr
210                 215                 220 gtt acc ggg gcg ctg gca ttt gcc att acg cgc gga ctg aac aag cgc         720
Val Thr Gly Ala Leu Ala Phe Ala Ile Thr Arg Gly Leu Asn Lys Arg
225                 230                 235                 240 gtg aag ctg ttc ctc tgc tgt gcg gat aac ctg att agc ggc aat gcg         768
Val Lys Leu Phe Leu Cys Cys Ala Asp Asn Leu Ile Ser Gly Asn Ala
                245                 250                 255 ttc aag ctg ggc gat atc atc acc tat cgc aac ggt aaa aaa gtt gaa         816
Phe Lys Leu Gly Asp Ile Ile Thr Tyr Arg Asn Gly Lys Lys Val Glu
        260                 265                 270 gtg atg aac act gat gcc gaa ggg cgt ctg gtg ctt gcc gat ggt ctg         864
Val Met Asn Thr Asp Ala Glu Gly Arg Leu Val Leu Ala Asp Gly Leu
        275                 280                 285 att gat gcc agt gcg cag aaa ccg gaa atg atc att gat gcg gcg acc         912
Ile Asp Ala Ser Ala Gln Lys Pro Glu Met Ile Ile Asp Ala Ala Thr
290                 295                 300 ctc acc ggg gcg gcg aaa act gcg ctg ggt aat gat tat cac gcg ctg         960
Leu Thr Gly Ala Ala Lys Thr Ala Leu Gly Asn Asp Tyr His Ala Leu
305                 310                 315                 320 ttc agt ttt gac gat gcg ctg gcc ggt cgc ttg ctg gcg agt gcc gcg        1008
Phe Ser Phe Asp Asp Ala Leu Ala Gly Arg Leu Leu Ala Ser Ala Ala
                325                 330                 335 cag gag aac gaa ccg ttc tgg cgt ctg ccg ctg gcg gag ttc cac cgc        1056
Gln Glu Asn Glu Pro Phe Trp Arg Leu Pro Leu Ala Glu Phe His Arg
        340                 345                 350 agc cag ctg ccg tct aac ttt gcc gaa ctg aac aat acc gga agc gcg        1104
Ser Gln Leu Pro Ser Asn Phe Ala Glu Leu Asn Asn Thr Gly Ser Ala
        355                 360                 365 gcg tat ccg gca ggc gcg agc acg gcg gcg ggc ttc ctg tcg cac ttt        1152
Ala Tyr Pro Ala Gly Ala Ser Thr Ala Ala Gly Phe Leu Ser His Phe
370                 375                 380 gtt gag aac tat cag caa ggc tgg ctg cat atc gac tgc tcg gcg act        1200
Val Glu Asn Tyr Gln Gln Gly Trp Leu His Ile Asp Cys Ser Ala Thr
385                 390                 395                 400 tac cgt aaa gcg ccg gtt gaa cag tgg tct gcg ggc gct acg gga ctt        1248
Tyr Arg Lys Ala Pro Val Glu Gln Trp Ser Ala Gly Ala Thr Gly Leu
                405                 410                 415
```

```
ggt gtg cgc acg ata gct aat ctg tta acg gcg taa              1284
Gly Val Arg Thr Ile Ala Asn Leu Leu Thr Ala
        420                 425
```

<210> SEQ ID NO 8
<211> LENGTH: 427
<212> TYPE: PRT
<213> ORGANISM: Escherichia coli

<400> SEQUENCE: 8

```
Met Thr Glu Ala Met Lys Ile Thr Leu Ser Thr Gln Pro Ala Asp Ala
1               5                   10                  15

Arg Trp Gly Glu Lys Ala Thr Tyr Ser Ile Asn Asn Asp Gly Ile Thr
            20                  25                  30

Leu His Leu Asn Gly Ala Asp Asp Leu Gly Leu Ile Gln Arg Ala Ala
        35                  40                  45

Arg Lys Ile Asp Gly Leu Gly Ile Lys His Val Gln Leu Ser Gly Glu
    50                  55                  60

Gly Trp Asp Ala Asp Arg Cys Trp Ala Phe Trp Gln Gly Tyr Lys Ala
65                  70                  75                  80

Pro Lys Gly Thr Arg Lys Val Val Trp Pro Asp Leu Asp Asp Ala Gln
            85                  90                  95

Arg Gln Glu Leu Asp Asn Arg Leu Met Ile Ile Asp Trp Val Arg Asp
            100                 105                 110

Thr Ile Asn Ala Pro Ala Glu Glu Leu Gly Pro Ser Gln Leu Ala Gln
        115                 120                 125

Arg Ala Val Asp Leu Ile Ser Asn Val Ala Gly Asp Arg Val Thr Tyr
    130                 135                 140

Arg Ile Thr Lys Gly Glu Asp Leu Arg Glu Gln Gly Tyr Met Gly Leu
145                 150                 155                 160

His Thr Val Gly Arg Gly Ser Glu Arg Ser Pro Val Leu Leu Ala Leu
                165                 170                 175

Asp Tyr Asn Pro Thr Gly Asp Lys Glu Ala Pro Val Tyr Ala Cys Leu
            180                 185                 190

Val Gly Lys Gly Ile Thr Phe Asp Ser Gly Gly Tyr Ser Ile Lys Gln
        195                 200                 205

Thr Ala Phe Met Asp Ser Met Lys Ser Asp Met Gly Gly Ala Ala Thr
    210                 215                 220

Val Thr Gly Ala Leu Ala Phe Ala Ile Thr Arg Gly Leu Asn Lys Arg
225                 230                 235                 240

Val Lys Leu Phe Leu Cys Cys Ala Asp Asn Leu Ile Ser Gly Asn Ala
                245                 250                 255

Phe Lys Leu Gly Asp Ile Ile Thr Tyr Arg Asn Gly Lys Lys Val Glu
            260                 265                 270

Val Met Asn Thr Asp Ala Glu Gly Arg Leu Val Leu Ala Asp Gly Leu
        275                 280                 285

Ile Asp Ala Ser Ala Gln Lys Pro Glu Met Ile Ile Asp Ala Ala Thr
    290                 295                 300

Leu Thr Gly Ala Ala Lys Thr Ala Leu Gly Asn Asp Tyr His Ala Leu
305                 310                 315                 320

Phe Ser Phe Asp Asp Ala Leu Ala Gly Arg Leu Leu Ala Ser Ala Ala
                325                 330                 335

Gln Glu Asn Glu Pro Phe Trp Arg Leu Pro Leu Ala Glu Phe His Arg
            340                 345                 350

Ser Gln Leu Pro Ser Asn Phe Ala Glu Leu Asn Asn Thr Gly Ser Ala
```

```
                355                 360                 365
Ala Tyr Pro Ala Gly Ala Ser Thr Ala Ala Gly Phe Leu Ser His Phe
            370                 375                 380

Val Glu Asn Tyr Gln Gln Gly Trp Leu His Ile Asp Cys Ser Ala Thr
385                 390                 395                 400

Tyr Arg Lys Ala Pro Val Glu Gln Trp Ser Ala Gly Ala Thr Gly Leu
                405                 410                 415

Gly Val Arg Thr Ile Ala Asn Leu Leu Thr Ala
            420                 425

<210> SEQ ID NO 9
<211> LENGTH: 1458
<212> TYPE: DNA
<213> ORGANISM: Escherichia coli
<220> FEATURE:
<221> NAME/KEY: CDS
<222> LOCATION: (1)..(1458)

<400> SEQUENCE: 9 gtg tct gaa ctg tct caa tta tct cca cag ccg ctg tgg gat att ttt      48
Val Ser Glu Leu Ser Gln Leu Ser Pro Gln Pro Leu Trp Asp Ile Phe
1               5                   10                  15 gcc aaa atc tgt tct att cct cac ccg tcc tat cat gaa gag caa ctc      96
Ala Lys Ile Cys Ser Ile Pro His Pro Ser Tyr His Glu Glu Gln Leu
                20                  25                  30 gct gaa tac att gtt ggt tgg gca aaa gag aaa ggt ttc cat gtc gaa     144
Ala Glu Tyr Ile Val Gly Trp Ala Lys Glu Lys Gly Phe His Val Glu
            35                  40                  45 cgc gat cag gta ggt aat atc ctg att cgt aaa cct gct acc gca ggt     192
Arg Asp Gln Val Gly Asn Ile Leu Ile Arg Lys Pro Ala Thr Ala Gly
        50                  55                  60 atg gaa aat cgt aaa ccg gtc gtc tta cag gcc cac ctc gat atg gtg     240
Met Glu Asn Arg Lys Pro Val Val Leu Gln Ala His Leu Asp Met Val
65                  70                  75                  80 ccg cag aaa aat aac gac acc gtg cat gac ttc acg aaa gat cct atc     288
Pro Gln Lys Asn Asn Asp Thr Val His Asp Phe Thr Lys Asp Pro Ile
                85                  90                  95 cag cct tat att gat ggc gaa tgg gtt aaa gcg cgc ggc acc acg ctg     336
Gln Pro Tyr Ile Asp Gly Glu Trp Val Lys Ala Arg Gly Thr Thr Leu
            100                 105                 110 ggt gcg gat aac ggc att ggt atg gcc tct gcg ctg gcg gtt ctg gct     384
Gly Ala Asp Asn Gly Ile Gly Met Ala Ser Ala Leu Ala Val Leu Ala
        115                 120                 125 gac gaa aac gtg gtt cac ggc ccg ctg gaa gtg ctg acc atg acc     432
Asp Glu Asn Val Val His Gly Pro Leu Glu Val Leu Thr Met Thr
130                 135                 140 gaa gaa gcc ggt atg gac ggt gcg ttc ggc tta cag ggc aac tgg ttg     480
Glu Glu Ala Gly Met Asp Gly Ala Phe Gly Leu Gln Gly Asn Trp Leu
145                 150                 155                 160 cag gct gat att ctg att aac acc gac tcc gaa gaa gaa ggt gaa atc     528
Gln Ala Asp Ile Leu Ile Asn Thr Asp Ser Glu Glu Glu Gly Glu Ile
                165                 170                 175 tac atg ggt tgt gcg ggg ggt atc gac ttc acc tcc aac ctg cat tta     576
Tyr Met Gly Cys Ala Gly Gly Ile Asp Phe Thr Ser Asn Leu His Leu
            180                 185                 190 gat cgt gaa gcg gtt cca gct ggt ttt gaa acc ttc aag tta acc tta     624
Asp Arg Glu Ala Val Pro Ala Gly Phe Glu Thr Phe Lys Leu Thr Leu
        195                 200                 205 aaa ggt ctg aaa ggc ggt cac tcc ggc ggg gaa atc cac gtt ggg ctg     672
Lys Gly Leu Lys Gly Gly His Ser Gly Gly Glu Ile His Val Gly Leu
210                 215                 220
```

```
ggt aat gcc aac aaa ctg ctg gtg cgc ttc ctg gcg ggt cat gcg gaa      720
Gly Asn Ala Asn Lys Leu Leu Val Arg Phe Leu Ala Gly His Ala Glu
225                 230                 235                 240 gaa ctg gat ctg cgc ctt atc gat ttc aac ggc ggc aca ctg cgt aac      768
Glu Leu Asp Leu Arg Leu Ile Asp Phe Asn Gly Gly Thr Leu Arg Asn
            245                 250                 255 gcc atc ccg cgt gaa gcc ttt gcg acc att gct gtc gca gct gat aaa      816
Ala Ile Pro Arg Glu Ala Phe Ala Thr Ile Ala Val Ala Ala Asp Lys
        260                 265                 270 gtc gac gtc ctg aaa tct ctg gtg aat acc tat cag gag atc ctg aaa      864
Val Asp Val Leu Lys Ser Leu Val Asn Thr Tyr Gln Glu Ile Leu Lys
    275                 280                 285 aac gag ctg gca gaa aaa gag aaa aat ctg gcc ttg ttg ctg gac tct      912
Asn Glu Leu Ala Glu Lys Glu Lys Asn Leu Ala Leu Leu Leu Asp Ser
290                 295                 300 gta gcg aac gat aaa gct gcc ctg att gcg aaa tct cgc gat acc ttt      960
Val Ala Asn Asp Lys Ala Ala Leu Ile Ala Lys Ser Arg Asp Thr Phe
305                 310                 315                 320 att cgt ctg ctg aac gcc acc ccg aac ggt gtg att cgt aac tcc gat     1008
Ile Arg Leu Leu Asn Ala Thr Pro Asn Gly Val Ile Arg Asn Ser Asp
            325                 330                 335 gta gcc aaa ggt gtg gtt gaa acc tcc ctg aac gtc ggt gtg gtg acc     1056
Val Ala Lys Gly Val Val Glu Thr Ser Leu Asn Val Gly Val Val Thr
        340                 345                 350 atg act gac aat aac gta gaa att cac tgc ctg atc cgt tca ctg atc     1104
Met Thr Asp Asn Asn Val Glu Ile His Cys Leu Ile Arg Ser Leu Ile
    355                 360                 365 gac agc ggt aaa gac tac gtg gtg agc atg ctg gat tcg ctg ggt aaa     1152
Asp Ser Gly Lys Asp Tyr Val Val Ser Met Leu Asp Ser Leu Gly Lys
370                 375                 380 ctg gct ggc gcg aaa acc gaa gcg aaa ggc gca tat cct ggc tgg cag     1200
Leu Ala Gly Ala Lys Thr Glu Ala Lys Gly Ala Tyr Pro Gly Trp Gln
385                 390                 395                 400 ccg gac gct aat tct ccg gtg atg cat ctg gta cgt gaa acc tat cag     1248
Pro Asp Ala Asn Ser Pro Val Met His Leu Val Arg Glu Thr Tyr Gln
            405                 410                 415 cgc ctg ttc aac aag acg ccg aac atc cag att atc cac gcg ggc ctg     1296
Arg Leu Phe Asn Lys Thr Pro Asn Ile Gln Ile Ile His Ala Gly Leu
        420                 425                 430 gaa tgt ggt ctg ttc aaa aaa ccg tat ccg gaa atg gac atg gtt tct     1344
Glu Cys Gly Leu Phe Lys Lys Pro Tyr Pro Glu Met Asp Met Val Ser
    435                 440                 445 atc ggg cca act atc acc ggt cca cac tct ccg gat gag caa gtt cac     1392
Ile Gly Pro Thr Ile Thr Gly Pro His Ser Pro Asp Glu Gln Val His
450                 455                 460 atc gaa agc gta ggt cat tac tgg aca ctg ctg act gaa ctg ctg aaa     1440
Ile Glu Ser Val Gly His Tyr Trp Thr Leu Leu Thr Glu Leu Leu Lys
465                 470                 475                 480 gaa att ccg gcg aag taa                                             1458
Glu Ile Pro Ala Lys
            485

<210> SEQ ID NO 10
<211> LENGTH: 485
<212> TYPE: PRT
<213> ORGANISM: Escherichia coli

<400> SEQUENCE: 10

Val Ser Glu Leu Ser Gln Leu Ser Pro Gln Pro Leu Trp Asp Ile Phe
1               5                   10                  15
```

-continued

```
Ala Lys Ile Cys Ser Ile Pro His Pro Ser Tyr His Glu Glu Gln Leu
             20                  25                  30

Ala Glu Tyr Ile Val Gly Trp Ala Lys Glu Lys Gly Phe His Val Glu
         35                  40                  45

Arg Asp Gln Val Gly Asn Ile Leu Ile Arg Lys Pro Ala Thr Ala Gly
 50                  55                  60

Met Glu Asn Arg Lys Pro Val Val Leu Gln Ala His Leu Asp Met Val
65                  70                  75                  80

Pro Gln Lys Asn Asn Asp Thr Val His Asp Phe Thr Lys Asp Pro Ile
                 85                  90                  95

Gln Pro Tyr Ile Asp Gly Glu Trp Val Lys Ala Arg Gly Thr Thr Leu
            100                 105                 110

Gly Ala Asp Asn Gly Ile Gly Met Ala Ser Ala Leu Ala Val Leu Ala
        115                 120                 125

Asp Glu Asn Val Val His Gly Pro Leu Glu Val Leu Leu Thr Met Thr
    130                 135                 140

Glu Glu Ala Gly Met Asp Gly Ala Phe Gly Leu Gln Gly Asn Trp Leu
145                 150                 155                 160

Gln Ala Asp Ile Leu Ile Asn Thr Asp Ser Glu Glu Gly Glu Ile
                165                 170                 175

Tyr Met Gly Cys Ala Gly Gly Ile Asp Phe Thr Ser Asn Leu His Leu
            180                 185                 190

Asp Arg Glu Ala Val Pro Ala Gly Phe Glu Thr Phe Lys Leu Thr Leu
        195                 200                 205

Lys Gly Leu Lys Gly Gly His Ser Gly Gly Glu Ile His Val Gly Leu
    210                 215                 220

Gly Asn Ala Asn Lys Leu Leu Val Arg Phe Leu Ala Gly His Ala Glu
225                 230                 235                 240

Glu Leu Asp Leu Arg Leu Ile Asp Phe Asn Gly Gly Thr Leu Arg Asn
                245                 250                 255

Ala Ile Pro Arg Glu Ala Phe Ala Thr Ile Ala Val Ala Ala Asp Lys
            260                 265                 270

Val Asp Val Leu Lys Ser Leu Val Asn Thr Tyr Gln Glu Ile Leu Lys
        275                 280                 285

Asn Glu Leu Ala Glu Lys Glu Lys Asn Leu Ala Leu Leu Leu Asp Ser
    290                 295                 300

Val Ala Asn Asp Lys Ala Ala Leu Ile Ala Lys Ser Arg Asp Thr Phe
305                 310                 315                 320

Ile Arg Leu Leu Asn Ala Thr Pro Asn Gly Val Ile Arg Asn Ser Asp
                325                 330                 335

Val Ala Lys Gly Val Val Glu Thr Ser Leu Asn Val Gly Val Val Thr
            340                 345                 350

Met Thr Asp Asn Asn Val Glu Ile His Cys Leu Ile Arg Ser Leu Ile
        355                 360                 365

Asp Ser Gly Lys Asp Tyr Val Val Ser Met Leu Asp Ser Leu Gly Lys
    370                 375                 380

Leu Ala Gly Ala Lys Thr Glu Ala Lys Gly Ala Tyr Pro Gly Trp Gln
385                 390                 395                 400

Pro Asp Ala Asn Ser Pro Val Met His Leu Val Arg Glu Thr Tyr Gln
                405                 410                 415

Arg Leu Phe Asn Lys Thr Pro Asn Ile Gln Ile Ile His Ala Gly Leu
            420                 425                 430

Glu Cys Gly Leu Phe Lys Lys Pro Tyr Pro Glu Met Asp Met Val Ser
        435                 440                 445
```

Ile Gly Pro Thr Ile Thr Gly Pro His Ser Pro Asp Glu Gln Val His
    450                 455                 460

Ile Glu Ser Val Gly His Tyr Trp Thr Leu Leu Thr Glu Leu Leu Lys
465                 470                 475                 480

Glu Ile Pro Ala Lys
            485

<210> SEQ ID NO 11
<211> LENGTH: 64
<212> TYPE: DNA
<213> ORGANISM: Artificial sequence
<220> FEATURE:
<223> OTHER INFORMATION: primer pepA1

<400> SEQUENCE: 11
atctgtagcc accgccgttg tctttaagat tcaggagcgt agtgctgaag cctgcttttt    60
tata                                                                64

<210> SEQ ID NO 12
<211> LENGTH: 63
<212> TYPE: DNA
<213> ORGANISM: Artificial sequence
<220> FEATURE:
<223> OTHER INFORMATION: primer pepA2

<400> SEQUENCE: 12
aggcgttcac gccgcatccg gcaataacag ccttgcctga cgcaacgctc aagttagtat    60
aaa                                                                 63

<210> SEQ ID NO 13
<211> LENGTH: 62
<212> TYPE: DNA
<213> ORGANISM: Artificial sequence
<220> FEATURE:
<223> OTHER INFORMATION: primer pepB1

<400> SEQUENCE: 13
acctgcaata ctgttttgcg ggtgatcgac aaggagactt aactgaagcc tgcttttta    60 ta                                                                  62

<210> SEQ ID NO 14
<211> LENGTH: 62
<212> TYPE: DNA
<213> ORGANISM: Artificial sequence
<220> FEATURE:
<223> OTHER INFORMATION: primer pepB2

<400> SEQUENCE: 14
acgccgttaa cagattagct atcgtgcgca caccaagtcc cgtacgctca agttagtata    60
aa                                                                  62

<210> SEQ ID NO 15
<211> LENGTH: 62
<212> TYPE: DNA
<213> ORGANISM: Artificial sequence
<220> FEATURE:
<223> OTHER INFORMATION: primer pepD1

<400> SEQUENCE: 15
acctgcaata ctgttttgcg ggtgatcgac aaggagactt aactgaagcc tgcttttta    60 ta                                                                  62

```
<210> SEQ ID NO 16
<211> LENGTH: 61
<212> TYPE: DNA
<213> ORGANISM: Artificial sequence
<220> FEATURE:
<223> OTHER INFORMATION: primer pepD2

<400> SEQUENCE: 16
caaatcaaat aattacttcg ccggaatttc tttcagcagt tcacgctcaa gttagtataa       60
a                                                                      61
```

METHOD FOR PRODUCING AN L-AMINO ACID USING A BACTERIUM OF THE ENTEROBACTERIACEAE FAMILY, HAVING ATTENUATED EXPRESSION OF GENE(S) ENCODING PEPTIDASE

This application is a Continuation of, and claims priority under 35 U.S.C. §120 to, International Application No. PCT/JP2011/063301, filed Jun. 3, 2011, and claims priority therethrough under 35 U.S.C. §119 to Russian Patent Application No. 2010122647, filed Jun. 3, 2010, the entireties of which are incorporated by reference herein. Also, the Sequence Listing filed electronically herewith is hereby incorporated by reference (File name: 2012-11-28T_US-431_Seq_List; File size: 35 KB; Date recorded: 2012-11-28).

FIELD OF THE INVENTION

The present invention relates to the microbiological industry, and specifically to a method for producing L-amino acids, such as L-arginine, L-citrulline, and L-lysine. The method uses a bacterium of the Enterobacteriaceae family which has been modified to attenuate expression of gene(s) encoding peptidase.

BRIEF DESCRIPTION OF THE RELATED ART

Conventionally, L-amino acids are industrially produced by fermentation methods utilizing strains of microorganisms from natural sources, or mutants thereof. Typically, the microorganisms are modified to enhance production yields of L-amino acids.

Many techniques to enhance L-amino acid production yields have been reported, including by transforming microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition caused by the produced L-amino acid (see, for example, WO 95/16042 or U.S. Pat. Nos. 4,346,170; 5,661,012 and 6,040,160).

Other ways to enhance L-amino acid production yields is to attenuate expression of a gene or several genes which are involved in the degradation of the target L-amino acid, genes which divert the precursors of the target L-amino acid from the L-amino acid biosynthetic pathway, genes involved in the redistribution of the carbon, nitrogen, and phosphate fluxes, and genes coding for toxins, etc.

The pepA gene (synonym carP) from *Escherichia coli* encodes the multifunctional enzyme aminopeptidase A (PepA), which combines catalytic and regulatory properties. It has been shown that, apart from hydrolysis of N-terminal amino acid residues of proteins, aminopeptidase A is required for the site-specific DNA recombination and monomerization of plasmid multimers (Stirling et al. (1989) EMBO J., 8, 1623-1627; Charlier et al (1995) J. Mol. Biol., 250, 392-406). Another aminopeptidase A function is transcriptional regulation. PepA is a DNA binding protein and is involved in the transcriptional repression of the carAB operon, which controls the synthesis of carbamoyl phosphate synthase (Roovers et al, (1988) J. Mol. Biol., 204, 857-865). Carbamoyl phosphate is an intermediate of L-arginine and pyrimidine biosynthetic pathways. Interaction between carbamoyl phosphate and L-ornithine results in L-citrulline formation, which is converted to L-arginine via L-argininosuccinate.

The pepB gene (synonyms yhfI, b2523, ECK2520) from *Escherichia coli* encodes aminopeptidase B (PepB), which is one of four cysteinylglycinases in *E. coli*. Aminopeptidase B cleaves Leu-Gly, Leu-Gly-Gly, Cys-Gly, and Leu-Gly in vitro (Miller et al. (1994) Journal of Bacteriology, 176, 610-619, Hermsdorf et al. (1979) International Journal of Peptide and Protein Research, 13, 146-151, Suzuki et al (2001) Bioscience. Biotechnology. Biochemistry., 5, 1549-1558.) In vivo, aminopeptidase B is, along with aminopeptidases A and N, and dipeptidase D, one of four cysteinylglycinases (Suzuki et al., (2001) Journal of Bacteriology 2001; 183(4) 1489-1490). Divalent cations, including some that are not effective stimulators of activity, stabilize aminopeptidase B against heat inactivation (Suzuki et al (2001) Bioscience. Biotechnology. Biochemistry., 5, 1549-1558.).

The pepD gene (synonyms pepH, carnosinase) from *Escherichia coli* encodes peptidase D, which is a dipeptidase capable of breaking down a number of dipeptides with unblocked N termini, including cysteinylglycine (Schroeder et al., (1994) FEMS Microbiology Letters, 123, 153-159, Suzuki et al., (2001) Journal of Bacteriology, 183, 1489-1490). Peptidase D functions as a dimer of PepD monomers (Klein et al., (1986) Journal of General Microbiology, 132, 2337-2343). Transcription of pepD increases five fold during phosphate starvation (Henrich et al., (1992) Molecular General Genetics, 232, 117-125).

But currently, there have been no reports of attenuating expression of the gene(s) encoding peptidase for production of L-amino acids, such as L-arginine, L-citrulline, and L-lysine.

SUMMARY OF THE INVENTION

Aspects of the present invention include enhancing the productivity of strains which are able to produce L-amino acids, such as L-arginine, L-citrulline, or L-lysine, and providing a method for producing such an L-amino acid using these strains.

The above aspects were achieved by finding that inactivation of a gene encoding peptidase, pepA, pepB, and/or pepD, can enhance production of L-amino acids, such as L-arginine, and L-lysine. Furthermore, since L-citrulline is an intermediate in the L-arginine biosynthetic pathway, production of this L-amino acid can also be enhanced.

The present invention provides a bacterium of the Enterobacteriaceae family having an increased ability to produce an L-amino acid such as L-arginine and L-citrulline.

It is an aspect of the present invention to provide a bacterium of the Enterobacteriaceae family having the ability to produce L-amino acid, wherein said bacterium has been modified to attenuate expression of a gene selected from the group consisting of pepA, pepB, pepD, and combinations thereof.

It is a further aspect of the present invention to provide the bacterium as described above, wherein expression of the gene(s) is/are attenuated by inactivation of the gene(s).

It is a further aspect of the present invention to provide the bacterium as described above, wherein the bacterium belongs to the genus *Escherichia*.

It is a further aspect of the present invention to provide the bacterium according to claim 3, wherein said bacterium is *Escherichia coli*.

It is a further aspect of the present invention to provide the bacterium as described above, wherein the bacterium belongs to the genus *Pantoea*.

It is a further aspect of the present invention to provide the bacterium as described above, wherein the L-amino acid is selected from the group consisting of L-arginine, L-citrulline, and L-lysine.

It is a further aspect of the present invention to provide the bacterium as described above, wherein the bacterium has been modified to attenuate expression of pepA, pepB, and pepD genes, and the L-amino acid is L-lysine.

It is a further aspect of the present invention to provide a method for producing an L-amino acid comprising:

cultivating the bacterium as described above in a medium, and collecting the L-amino acid from the culture medium.

It is a further aspect of the present invention to provide a method as described above, wherein said L-amino acid is selected from the group consisting of L-arginine, L-citrulline, and L-lysine.

DESCRIPTION OF THE PREFERRED EMBODIMENTS

Figure 1:
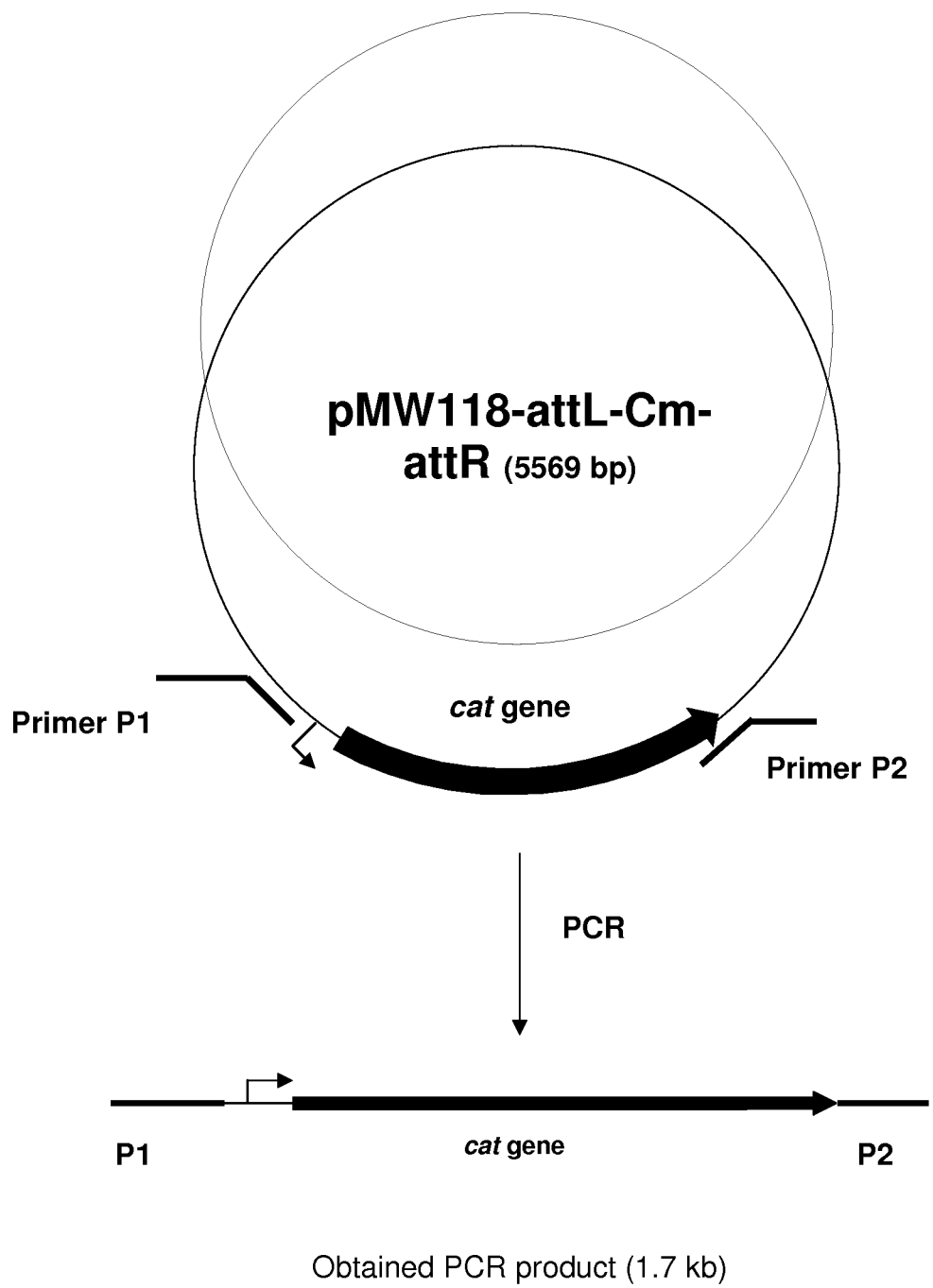
FIG. 1 shows the relative positions of primers P1 and P2 on plasmid pMW118-attL-Cm-attR.

The present invention is described in detail below.

1. Bacterium

The bacterium in accordance with the presently disclosed subject matter is a bacterium of the Enterobacteriaceae family having ability to produce L-amino acid, such as L-arginine, L-citrulline, or L-lysine, wherein the bacterium has been modified to attenuate expression of one or more genes encoding an aminopeptidase, such as the pepA, pepB, and/or pepD genes.

The term "bacterium having ability to produce an L-amino acid" can mean a bacterium which is able to produce and secrete L-amino acid into a medium, when the bacterium is cultured in the medium.

The term "bacterium having ability to produce an L-amino acid" also can mean a bacterium which is able to produce and cause accumulation of L-amino acid such as L-arginine, L-citrulline, or L-lysine in a culture medium in an amount larger than a wild-type or parental strain of *E. coli*, such as *E. coli* K-12, and can mean that the microorganism is able to cause accumulation in a medium of an amount not less than 0.5 g/L, in another example not less than 1.0 g/L of L-amino acid. The term "L-amino acid" can include L-arginine, L-citrulline, and L-lysine.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella Yersinia*, etc. Specifically, those classified as Enterobacteriaceae according to the taxonomy used in the NCBI (National Center for Biotechnology Information) database (www.ncbi.nlm.nih.gov/Taxonomy/Browser/wwwtax.cgi?id=543) can be used. A bacterium belonging to the genus *Escherichia* or *Pantoea* are particular examples.

The phrase "a bacterium belonging to the genus *Escherichia*" can mean that the bacterium is classified in the genus *Escherichia* according to the classification known to a person skilled in the art of microbiology. An example of a bacterium belonging to the genus *Escherichia* is, but is not limited to, *Escherichia coli* (*E. coli*). The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) can be used.

The phrase "a bacterium belonging to the genus *Pantoea*" can mean that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on nucleotide sequence analysis of 16S rRNA, etc.

The phrase "bacterium has been modified to attenuate expression of pepA gene encoding aminopeptidase A" can mean that the bacterium has been modified in such a way that the modified bacterium contains a reduced amount of the aminopeptidase A, or it can also mean that the bacterium is unable to synthesize the aminopeptidase A.

The phrase "bacterium has been modified to attenuate expression of pepB gene encoding aminopeptidase B" can mean that the bacterium has been modified in such a way that the modified bacterium contains a reduced amount of the aminopeptidase B, or it can also mean that the bacterium is unable to synthesize the aminopeptidase B.

The phrase "bacterium has been modified to attenuate expression of pepD gene encoding dipeptidase D" can mean that the bacterium has been modified in such a way that the modified bacterium contains a reduced amount of the dipeptidase D, or it can also mean that the bacterium is unable to synthesize the dipeptidase D.

The phrase "inactivation of a gene" can mean that the modified gene encodes a completely non-functional protein. It is also possible that the modified DNA region is unable to naturally express the gene due to the deletion of a part of the gene, the shifting of the reading frame of the gene, the introduction of missense/nonsense mutation(s), or the modification of an adjacent region of the gene, including sequences controlling gene expression, such as a promoter, enhancer, attenuator, ribosome-binding site, etc.

The presence or absence of a gene on the chromosome of a bacterium can be detected by well-known methods, including PCR, Southern blotting, and the like. In addition, the level of gene expression can be estimated by measuring the amount of mRNA transcribed from the gene using various well-known methods, including Northern blotting, quantitative RT-PCR, and the like. The amount of the protein encoded by the gene can be measured by well-known methods, including SDS-PAGE followed by an immunoblotting assay (Western blotting analysis), and the like.

The pepA gene (synonyms: carP, b4260, ECK4253) coding for aminopeptidase A from *Escherichia coli* has been elucidated (nucleotides complementary to nucleotides 4482463 to 4483974 in the sequence of GenBank Accession NC_000913.2). The pepA gene from *E. coli* is located on the chromosome between the holC and lptF genes. The nucleotide sequences of the pepA gene, and the amino acid sequence of PepA protein encoded by the pepA gene, are shown in SEQ ID NO: 1 and SEQ ID NO: 2, respectively.

The pepB gene (synonyms: yfhI, b2523, ECK2520) coding for aminopeptidase B from *Escherichia coli* has been elucidated (nucleotides complementary to nucleotides 2653097 to 2654380 in the sequence of GenBank Accession EG12310). The pepB gene from *E. coli* is located on the chromosome between the iscX and sseB genes. The nucleotide sequences of the pepB gene, and the amino acid sequence of PepB protein encoded by the pepB gene, are shown in SEQ ID NO: 7 and SEQ ID NO: 8, respectively.

The pepD gene (synonyms: pepH, b0237, ECK0238) coding for peptidase D from *Escherichia coli* has been elucidated (nucleotides complementary to nucleotides 254259 to 255716 in the sequence of GenBank Accession 10695). The pepD gene from *E. coli* is located on the chromosome between the gpt and prfH genes. The nucleotide sequences of the pepD gene, and the amino acid sequence of PepD protein encoded by the pepD gene, are shown in SEQ ID NO: 9 and SEQ ID NO: 10, respectively.

Since there may be some differences in DNA sequences between the genera or strains of the Enterobacteriaceae family, the gene to be inactivated on the chromosome is not limited to the gene shown in SEQ ID NO:1, 7, or 9, but may include genes homologous to SEQ ID No:1, 7, or 9, and which encode a variant protein. The phrase "variant protein" can mean a protein which has changes in the sequence, whether they are deletions, insertions, additions, or substitutions of amino acids, but still maintains the activity of the protein. The number of changes in the variant protein depends on the position in the three dimensional structure of the protein or the type of amino acid residues. It may be 1 to 30, in another example 1 to 15, and in another example 1 to 5. These changes in the variants can occur in regions of the protein which are not critical for the function of the protein. This is because some amino acids have high homology to one another so the three dimensional structure or activity is not affected by such a change. Therefore, the protein variant encoded by the gene may have a homology of not less than 80%, in another example not less than 90%, in another example not less than 95%, in another example not less than 98%, and in another example not less than 99%, with respect to the entire amino acid sequence shown in SEQ ID NO. 2, 8, or 10, as long as the protein prior to inactivation is able to function as aminopeptidase or dipeptidase. In this specification, the term "homology" can also refer to "identity".

Homology between two amino acid sequences can be determined using well-known methods, for example, the computer program BLAST 2.0, which calculates three parameters: score, identity, and similarity.

Moreover, the pepA, B, or D gene may be a variant, which hybridizes with the nucleotide sequence shown in SEQ ID NO: 1, 7, or 9, or a probe which can be prepared from the nucleotide sequence, under stringent conditions, provided that it encodes a functional protein prior to inactivation. "Stringent conditions" include those, under which a specific hybrid, for example, a hybrid having homology of not less than 60%, in another example not less than 70%, in another example not less than 80%, in another example not less than 90%, in another example not less than 95%, in another example not less than 98%, and in another example not less than 99% is formed and a non-specific hybrid, for example, a hybrid having homology lower than the above, is not formed. For example, stringent conditions are exemplified by washing one time, in another example two or three times at a salt concentration corresponding to 1×SSC, 0.1% SDS, or 0.1× SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Washing may be performed 2 to 3 times. The length of the probe may be suitably selected depending on the hybridization conditions, and is usually 100 bp to 1 kbp.

Expression of a gene can be attenuated by introducing a mutation into the gene on the chromosome so that the intracellular activity of the protein encoded by the gene is decreased as compared with an unmodified strain. Mutations which result in attenuation of expression of the gene include the replacement of one base or more to cause an amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the pepA gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein with decreased activity can be prepared, and the bacterium to be modified can be transformed with a DNA fragment containing the mutant gene. Then, the native gene on the chromosome is replaced with the mutant gene by homologous recombination, and the resulting strain can be selected. Gene replacement using homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by employing a plasmid containing a temperature-sensitive replication origin (U.S. Pat. No. 6,303, 383 or JP 05-007491A). Furthermore, site-specific mutation by gene substitution can also be incorporated using homologous recombination such as set forth above using a plasmid which is unable to replicate in the host.

Expression of the gene can also be attenuated by inserting a transposon or an IS factor into the coding region of the gene (U.S. Pat. No. 5,175,107), or by conventional methods, such as by mutagenesis with UV irradiation or nitrosoguanidine (N-methyl-N'-nitro-N-nitrosoguanidine), site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45), also called "Red-driven integration".

Methods for preparation of plasmid DNA, digestion and ligation of DNA, transformation, selection of oligonucleotides as primers, and the like may be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

L-Amino Acid-Producing Bacteria

Bacteria which are able to produce an L-amino acid such as L-arginine, L-citrulline, or L-lysine, may be employed.

The bacterium in accordance with the presently disclosed subject matter can be obtained by inactivating one or more genes encoding peptidase in a bacterium, which has a native or inherent ability to produce L-amino acid. Alternatively, the bacterium can be obtained by imparting the ability to produce L-amino acid to a bacterium already having an inactivated gene(s) encoding peptidase.

L-Arginine Producing Bacteria

Examples of L-arginine-producing bacteria or parent strains, which can be used to derive L-arginine-producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which the argA gene encoding N-acetylglutamate synthetase has been introduced (EP1170361A1), and the like.

Examples of parent strains which can be used to derive L-arginine producing bacteria also include strains in which expression of one or more genes encoding L-arginine biosynthetic enzymes is/are enhanced. Examples of such genes include the genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), argininosuccinic acid synthetase (argG), argininosuccinic acid lyase (argH), and carbamoyl phosphate synthetase (carAB). The abbreviations in parentheses after the enzyme names represent the gene names.

L-Citrulline Producing Bacteria

Examples of L-citrulline-producing bacteria or parent strains, which can be used to derive L-citrulline-producing bacteria belonging to the genus *Escherichia* include, but are not limited to, *E. coli* strains 333 (VKPM B-8084) and 374 (VKPM B-8086), both harboring mutant feedback-resistant carbamoyl phosphate synthetase (Russian Patent RU2264459 C2), strains *E. coli*, in which α-ketoglutarate synthase activity is increased, and ferredoxin NADP+ reductase, pyruvate synthase or α-ketoglutarate dehydrogenase activities are additionally modified (EP 2133417 A1), and strain *P. ananantis* NAlsucAsdhA, in which succinate dehydrogenase and α-ketoglutarate dehydrogenase activities are decreased (US Patent Application No 2009286290), and the like.

As L-citrulline is an intermediate of L-arginine biosynthetic pathway, examples of parent strains, which can be used to derive L-citrulline-producing bacteria, include strains, in which expression of one or more genes encoding an L-arginine biosynthetic enzyme is enhanced. Examples of such genes include, but are not limited to, genes encoding N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyltransferase (argF/I), and carbamoyl phosphate synthetase (carAB), or combinations thereof.

Examples of parent strains which can be used to derive L-citrulline-producing bacteria of the present invention can also include L-arginine-producing strains, in which activity of argininosuccinic acid synthetase (ArgG), which catalyzed conversion of L-citrulline to L-arginine, is reduced compared with parent strain. Activity of argininosuccinic acid synthetase can be decreased by inactivation of the corresponding gene argG by conventional methods as described above.

L-Lysine-Producing Bacteria

Examples of L-lysine-producing bacteria or parent strains belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred from the W3110 strain, which was derived from *Escherichia coli* K-12, by replacing the wild type lysC gene on the chromosome of the W3110 strain with a mutant lysC gene encoding a mutant aspartokinase III desensitized to feedback inhibition by L-lysine in which threonine at position 352 had been replaced with isoleucine, and conferring AEC resistance to the resulting strain (U.S. Pat. No. 5,661,012). The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive bacteria which are able to produce L-lysine also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

It is known that wild-type dihydrodipicolinate synthetase derived from *Escherichia coli* is subject to feedback inhibition by L-lysine, while wild-type aspartokinase derived from *Escherichia coli* is subject to suppression and feedback inhibition by L-lysine. Therefore, when the dapA and lysC genes are used, these genes can be mutant genes coding the enzymes that are not subject to the feedback inhibition by L-lysine.

Examples of DNA encoding a mutant dihydrodipicolinate synthetase desensitized to feedback inhibition by L-lysine include a DNA encoding a protein that has the amino acid sequence of the enzyme in which the histidine at position 118 is replaced by tyrosine. Examples of DNA encoding a mutant aspartokinase desensitized to feedback inhibition by L-lysine include a DNA encoding an AKIII having the amino acid sequence in which the threonine at position 352, the glycine at position 323, and the methionine at position 318 are replaced by isoleucine, asparagine and isoleucine, respectively (for these mutants, see U.S. Pat. No. 5,661,012 and U.S. Pat. No. 6,040,160). Such mutant DNAs can be obtained by site-specific mutagenesis using PCR or the like.

Wide host-range plasmids RSFD80, pCAB1, and pCABD2 are known as plasmids containing a mutant dapA gene encoding a mutant dihydrodipicolinate synthetase and a mutant lysC gene encoding a mutant aspartokinase (U.S. Pat. No. 6,040,160). *Escherichia coli* JM109 strain transformed with RSFD80 was named AJ12396 (U.S. Pat. No. 6,040,160), the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a known method.

Examples of parent strains which can be used to derive bacteria that are able to produce L-lysine also include strains having decreased or no activity of an enzyme that catalyzes a reaction that generates a compound other than L-lysine by branching off from the biosynthetic pathway of L-lysine. Examples of such enzymes include homoserine dehydrogenase, lysine decarboxylase (U.S. Pat. No. 5,827,698), and the malic enzyme (WO2005/010175). In order to reduce or eliminate the lysine decarboxylase activity, the expression of both the cadA gene and ldcC gene coding for lysine decarboxylase can be reduced (International Patent Publication WO2006/038695).

Examples of cadA- and ldcC genes-disrupted strain include the *Escherichia coli* WC196LC (WC196ΔcadAΔldc) strain. The WC196LC strain, which was designated AJ110692, was deposited at National Institute of Advanced Industrial Science and Technology, International Patent Organism Depositary (Central 6, 1-1, Higashi 1-Chome, Tsukuba-shi, Ibaraki-ken, 305-8566, Japan) on Oct. 7, 2008 as an international deposit, and assigned an accession number of FERM BP-11027.

1. Method of the Present Invention

Exemplary methods include producing an L-amino acid by cultivating the bacterium described herein in a culture medium to produce and secrete L-amino acid, such as L-arginine, L-citrulline, and/or L-lysine into the medium, and collecting L-amino acid from the medium.

The cultivation, collection, and purification of L-amino acid from the medium may be performed by conventional fermentation methods wherein an amino acid is produced using a bacterium.

The medium used for the culture may be either a synthetic or natural medium, so long as the medium includes a carbon source and a nitrogen source and minerals and, if necessary, appropriate amounts of nutrients which the chosen bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as by a shaking culture, and by a stirring culture with aeration, at a temperature of 20 to 40° C., or 30 to 38° C. The pH of the culture is usually between 5 and 9, or between 6.5 and 7.2. The pH of the culture can be adjusted with ammonia, calcium carbonate, various acids, various bases, and buffers. Usually, 1 to 5-day cultivation leads to accumulation of L-amino acid in the liquid medium.

After cultivation, solids such as cells can be removed from the liquid medium by centrifugation or membrane filtration, and then L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated PepA Gene

2. Deletion of the PepA Gene.

The pepA gene in a bacterial strain was deleted by the method initially developed by Datsenko, K. A. and Wanner, B. L. (Proc. Natl. Acad. Sci. USA, 2000, 97(12), 6640-6645) called "Red-driven integration". According to this procedure, the PCR primers P1 (SEQ ID NO: 3) and P2 (SEQ ID NO: 4), which are homologous to both the region adjacent to the pepA gene and the gene which confers antibiotic resistance in the template plasmid, were constructed. The plasmid pMW118-attL-Cm-attR (WO 05/010175) was used as the template in the PCR reaction. Conditions for PCR were as follows: initial DNA denaturation for 30 sec at 94° C., followed by 25 cycles of denaturation at 94° C. for 30 sec, annealing at 55° C. for 30 sec, elongation at 72° C. for 1 min 30 sec; and the final elongation for 2 min at 72° C.

The 1.7 kb PCR product (FIG. 1) was purified from an agarose gel and used for electroporation of the *E. coli* strain MG1655 (ATCC 700926), which contains the plasmid pKD46. The pKD46 plasmid (Datsenko, K. A. and Wanner, B. L., Proc. Natl. Acad. Sci. USA, 2000, 97:12:6640-45) contains a temperature-sensitive replication origin, and includes a 2,154 nucleotide DNA fragment of phage X (nucleotide positions 31088 to 33241, GenBank accession no. J02459), as well as the genes of the X Red homologous recombination system (γ, β, exo genes), which are under the control of the arabinose-inducible ParaB promoter. The pKD46 plasmid is necessary for integration of the PCR product into the chromosome of the MG1655 strain. The strain MG1655 can be obtained from American Type Culture Collection. (P.O. Box 1549 Manassas, Va. 20108, U.S.A.).

Electrocompetent cells were prepared as follows: *E. coli* MG1655/pKD46 cells were grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an OD600 of ≈0.6 and then were made electrocompetent by concentrating 100-fold and washing three times with ice-cold deionized H2O. Electroporation was performed using 70 µl of cells and ≈100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 µg/ml) and grown at 37° C. to select CmR recombinants. Then, to eliminate the pKD46 plasmid, two passages on L-agar with Cm at 42° C. were performed and the colonies were tested for sensitivity to ampicillin.

3. Verification of the PepA Gene Deletion by PCR.

Figure 2:
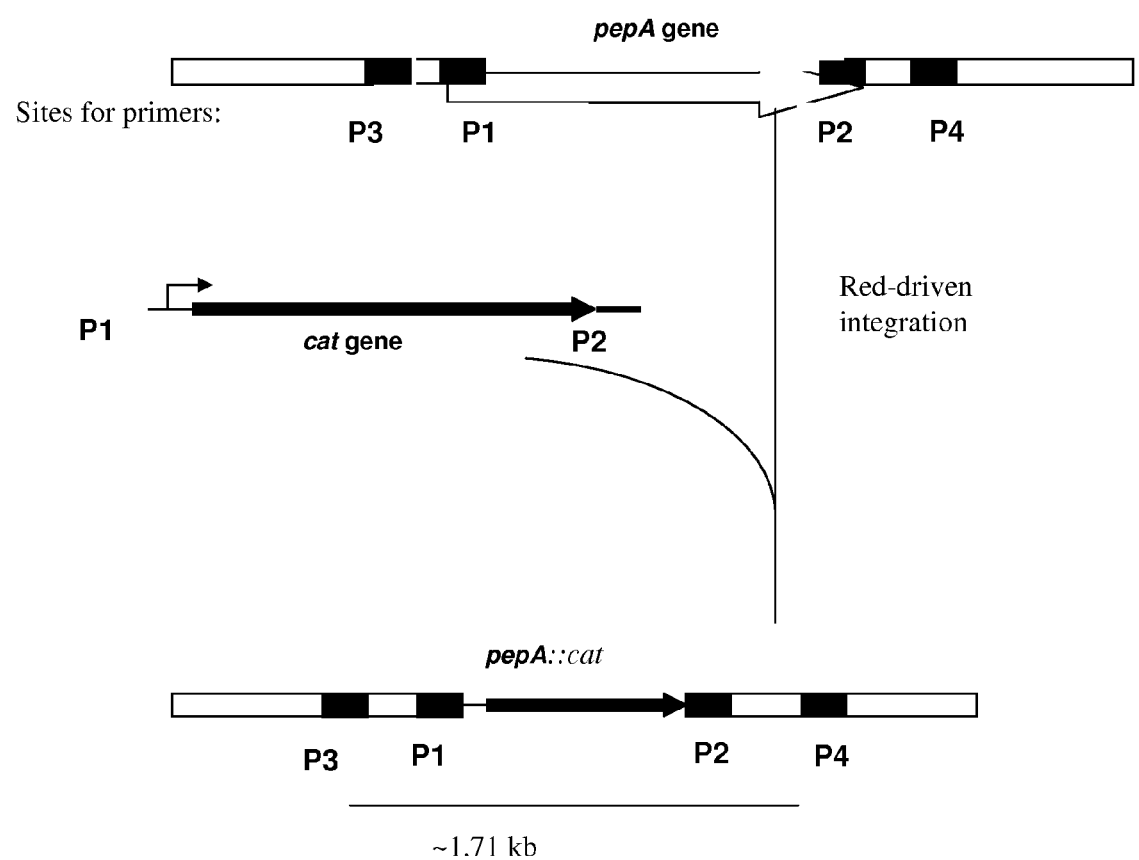
FIG. 2 shows the construction of the chromosomal DNA fragment which includes the inactivated pepA gene.

Mutants in which the pepA gene had been deleted were marked with a Cm resistance gene and were verified by PCR using the locus-specific primers P3 (SEQ ID NO: 5) and P4 (SEQ ID NO: 6). For this purpose, a freshly isolated colony was suspended in 20 µl water and then 1 µl of the suspension was used for PCR. Conditions for PCR were as follows: initial DNA denaturation for 30 sec at 94° C.; then 30 cycles of denaturation at 94° C. for 30 sec, annealing at 55° C. for 30 sec and elongation at 72° C. for 2 min; the final elongation for 2 min at 72° C. The PCR product obtained in the PCR reaction using the cells of the parent pepA+ strain MG1655 as the template was 1.65 kb in length. The PCR product obtained in the PCR reaction using the cells of the mutant MG1655 ΔpepA::cat strain as the template was 1.71 kb nucleotides in length (FIG. 2).

4. Elimination of Cm Resistance Gene (Cat Gene) from the Chromosome of *E. coli* Strain MG1655 ΔpepA::cat The Cm resistance gene was eliminated from the chromosome of the *E. coli* MG1655 pepA::cat strain using the int-xis system. For that purpose, *E. coli* strain MG1655 pepA::cat was transformed with pMWts-Int/X is plasmid (WO 05/010175). Transformant clones were selected on the LB-medium containing 100 μg/ml of ampicillin. Plates were incubated overnight at 30° C. Transformant clones were cured from the cat gene and pMWts-Int/X is plasmid by spreading the separate colonies at 37° C. (at this temperature repressor CIts is partially inactivated and transcription of the int/xis genes is derepressed) followed by selection of CmSApR variants. Elimination of the cat gene from the chromosome of the strain was verified by PCR with locus-specific primers P3 (SEQ ID NO: 5) and P4 (SEQ ID NO: 6). Conditions for PCR were as follows: initial DNA denaturation for 30 sec at 94° C.; then 30 cycles of denaturation at 94° C. for 30 sec, annealing at 55° C. for 30 sec and elongation at 72° C. for 2 min; the final elongation for 2 min at 72° C. The PCR product obtained in the reaction with the cells of MG1655ΔpepA::cat strain as a template, was 1.71 kb in length. The PCR product obtained in the reaction with cells without cat gene as a template was 160 bp in length. Thus, the strain with the inactivated pepA gene and cat gene deleted was obtained.

Example 2

Production of L-Arginine by *E. coli* Strain 382ΔPepA

To test the effect of inactivation of the pepA gene on L-arginine production, the DNA fragment from the chromosome of the above-described *E. coli* strain MG1655 ΔpepA was transferred to the L-arginine producing *E. coli* strain 382 by P1 transduction (Miller, J. H. (1972) Experiments in Molecular Genetics, Cold Spring Harbor Lab. Press, Plainview, N.Y.) to obtain the *E. coli* 382ΔpepA strain. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

*E. coli* strains, 382 and 382pepA, were separately cultivated with shaking at 37° C. for 18 hours in 3 ml of nutrient broth, and 0.3 ml of the cultures were inoculated into 2 ml of a fermentation medium in 20×200-mm test tubes and cultivated at 32° C. for 48 hours on a rotary shaker.

After the cultivation, the amount of L-arginine which has accumulated in the medium was determined by paper chromatography using the following mobile phase: butanol:acetic acid:water=4:1:1 (v/v). A solution of ninhydrin (2%) in acetone was used as a visualizing reagent. A spot containing L-arginine was cut out, the L-arginine was eluted with 0.5% water solution of CdCl2, and the amount of L-arginine was estimated spectrophotometrically at 540 nm.

The composition of the fermentation medium (g/l) is as follows:

| | |
|---|---|
| Glucose | 48.0 |
| (NH4)2SO4 | 35.0 |
| KH2PO4 | 2.0 |
| MgSO4•7H2O | 1.0 |
| Thiamine HCl | 0.0002 |
| Yeast extract | 1.0 |
| L-isoleucine | 0.1 |
| CaCO3 | 5.0 |

Glucose and magnesium sulfate are sterilized separately. CaCO3 is dry-heat sterilized at 180 C for 2 hours. The pH is adjusted to 7.0.

The results of test tube fermentations are shown in Table 1. As it can be seen from Table 1, the strain with an inactivated pepA gene was able to produce a higher amount of L-arginine as compared with the parent L-arginine producing *E. coli* strain 382.

TABLE 1

| Strain | Amount of L-arginine, g/l |
|---|---|
| 382 | 8.0 ± 0.2 |
| 382ΔpepA | 9.4 ± 0.7 |

Example 3

Production of Citrulline by *E. coli* Strain 382ΔPepA

To test the effect of inactivation of the pepA gene on L-arginine production, the DNA fragment from the chromosome of the above-described *E. coli* strain MG1655 ΔpepA can be transferred to *E. coli* citrulline-producing strain 382ΔargG by P1 transduction (Miller, J. H. (1972) Experiments in Molecular Genetics, Cold Spring Harbor Lab. Press, Plainview, N.Y.) to obtain *E. coli* 382ΔargGΔpepA strain. The strain 382ΔargG can be obtained by deletion of argG gene on the chromosome of 382 strain (VKPM B-7926) by the method initially developed by Datsenko, K. A. and Wanner, B. L. (Proc. Natl. Acad. Sci. USA, 2000, 97(12), 6640-6645) called "Red-driven integration". According to this procedure, the PCR primers homologous to both the region adjacent to the argG gene and the gene which confers antibiotic resistance in the template plasmid can be constructed. The plasmid pMW118-attL-Cm-attR (WO 05/010175) can be used as the template in the PCR reaction.

Both *E. coli* strains, 382ΔargG and 382ΔargGΔpepA, can be separately cultivated with shaking at 37° C. for 18 hours in 3 ml of nutrient broth, and 0.3 ml of the obtained cultures were inoculated into 2 ml of a fermentation medium in 20×200-mm test tubes and cultivated at 32° C. for 48 hours on a rotary shaker.

After the cultivation, the amount of citrulline which accumulates in the medium can be determined by paper chromatography using the following mobile phase: butanol:acetic acid:water=4:1:1 (v/v). A solution of ninhydrin (2%) in acetone can be used as a visualizing reagent. A spot containing citrulline can be cut out, citrulline can be eluted with 0.5% water solution of CdCl2, and the amount of citrulline can be estimated spectrophotometrically at 540 nm.

The composition of the fermentation medium (g/l) can be as follows:

| | |
|---|---|
| Glucose | 48.0 |
| (NH4)2SO4 | 35.0 |
| KH2PO4 | 2.0 |
| MgSO4•7H2O | 1.0 |
| Thiamine HCl | 0.0002 |
| Yeast extract | 1.0 |
| L-isoleucine | 0.1 |
| L-arginine | 0.1 |
| CaCO3 | 5.0 |

Glucose and magnesium sulfate are sterilized separately. CaCO3 is dry-heat sterilized at 180° C. for 2 hours. The pH is adjusted to 7.0.

Example 4

Construction of L-Lysine-Producing Bacterium Having Decreased Amino-Peptidase Activity Strains which do not express amino-peptidase A or B or D (WC196ΔcadAΔldcCΔpepA::Km, WC196ΔcadAΔldcCΔpepB::Km and WC196ΔcadAΔldcCΔpepD::Km strains) were constructed from the WC196ΔcadAΔldcC strain.

The WC196ΔcadAΔldcC strain is able to produce L-lysine and was used to derive the object pep gene-deficient strain. Each pep gene in WC196ΔcadAΔldcC was deleted by the method called "Red-driven integration", in similar manner shown in Example 1.

The pepA, pepB or pepD gene was deleted by using the primers of SEQ ID NOS: 11 and 12 for pepA, the primers of SEQ ID NOS: 13 and 14 for pepB, the primers of SEQ ID NOS: 15 and 16 for pepD, respectively. The WC196ΔcadAΔldcCΔpepA::Km, WC196ΔcadAΔldcCΔpepB::Km and WC196ΔcadAΔldcCΔpepD::Km strains in which each amino-peptidase gene was deleted, were thereby obtained. The cadA gene and the ldcC gene in the WC196196ΔcadAΔldcC strain may also be deleted in a similar manner.

Furthermore, each strain was cultured at 37° C. in L medium until the final OD600 of the culture became about 0.6. Then, an equal volume of a 40% glycerol solution was added to the culture, the mixture was stirred, and then divided into appropriate volumes and stored at −80° C. These are called glycerol stocks.

Example 5

Evaluation of L-Lysine Producing Ability of the Strain which Decreased Amino-Peptidase Activity Each of the glycerol stocks of the strains was thawed, and 100 μL of each was evenly applied to an L plate and cultured at 37° C. for 24 hours. The above glycerol stocks were thawed, and uniformly applied to an L-plate and culture was performed at 37° C. for 24 hours. The suspension of the obtained cells was diluted 101 times, OD620 value (n) of the diluted suspension was measured, and the cell suspension in a volume corresponding to 50/n was inoculated into 20 mL of a fermentation medium in a 500-mL Sakaguchi flask, and culture was performed at 37° C. for 48 hours on a reciprocally shaking culture machine (115 rpm). After the culture, amount of L-lysine accumulated in the medium was measured in a known manner (Biotec Analyzer AS210, SAKURA SEIKI).

The composition of the fermentation medium (g/l) is as follows:

Composition of L-Lysine Fermentation Medium:

| | |
|---|---|
| Glucose | 40 |
| (NH4)2SO4 | 24 |
| K2HPO4 | 1.0 |
| MgSO4•7H2O | 1.0 |
| FeSO4•7H2O | 0.01 |
| MnSO4•5H2O | 0.01 |
| Yeast extract | 2.0 |
| CaCO3 (Japanese Pharmacopoeia) | 30 |
| Distilled water | To final volume of 1 L |

The medium was adjusted to pH 7.0 with KOH, and autoclaved at 115° C. for 10 minutes. Glucose and MgSO4.7H2O were separately dry-heat sterilized at 180 C for 2 hours.

The results are shown in Table 2. The yield (%) represents the yield of L-lysine based on glucose. As it can be seen from Table 2, the WC196ΔcadAΔldcCΔpepA, WC196ΔcadAΔldcCΔpepB, WC196ΔcadAΔldcCΔpepD, strains were able to produce a higher amount of L-lysine as compared with the parent L-lysine producing *E. coli* strain WC196ΔcadAΔldcC.

TABLE 2

| CT48 | OD620 | Lys (g/L) | Glc (g/L) | Yield (%) |
|---|---|---|---|---|
| WC196 ΔcadA ΔldcC | 26.0 | 1.4 | 0.0 | 3.5 |
| WC196 ΔcadA ΔldcCΔpepA ::Km | 26.8 | 1.6 | 0.0 | 3.9 |
| WC196 ΔcadA ΔldcCΔpepB ::Km | 25.9 | 1.6 | 0.0 | 4.0 |
| WC196 ΔcadA ΔldcCΔpepD ::Km | 25.6 | 1.6 | 0.0 | 4.0 |

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of L-arginine, L-citrulline, and L-lysine by a bacterium of Enterobacteriaceae family can be improved.

The invention claimed is:

1. A method for producing an L-amino acid comprising:
cultivating a bacterium of the Enterobacteriaceae family having an ability to produce an L-amino acid in a culture medium; and
collecting the L-amino acid from the culture medium;
wherein said bacterium has been modified to attenuate expression of a gene selected from the group consisting of pepA, pepB, pepD, and combinations thereof; and
wherein the L-amino acid is selected from the group consisting of L-arginine, L-citruline, and L-lysine.

2. The method according to claim 1, wherein expression of the gene(s) is/are attenuated by inactivation of the gene(s).

3. The method according to claim 1, wherein said bacterium belongs to the genus *Escherichia*.

4. The method according to claim 3, wherein said bacterium is *Escherichia coli*.

5. The method according to claim 1, wherein said bacterium belongs to the genus *Pantoea*.

6. The method according to claim 1, wherein the bacterium has been modified to attenuate expression of pepA, pepB, and pepD genes, and the L-amino acid is L-lysine.

* * * * *